(12) United States Patent
Smith

(10) Patent No.: US 7,808,637 B2
(45) Date of Patent: *Oct. 5, 2010

(54) METHOD AND APPARATUS FOR DETERMINING LIQUID CRYSTAL CELL PARAMETERS FROM FULL MUELLER MATRIX MEASUREMENTS

(75) Inventor: Matthew Smith, Madison, AL (US)

(73) Assignee: Axometrics, Incorporated, Huntsville, AL (US)

( * ) Notice: Subject to any disclaimer, the term of this patent is extended or adjusted under 35 U.S.C. 154(b) by 312 days.

This patent is subject to a terminal disclaimer.

(21) Appl. No.: 11/921,745

(22) Filed: Dec. 7, 2007

(65) Prior Publication Data

US 2009/0296089 A1 Dec. 3, 2009

Related U.S. Application Data

(63) Continuation of application No. PCT/US2006/022313, filed on Jun. 9, 2006, which is a continuation-in-part of application No. 11/150,363, filed on Jun. 10, 2005, now Pat. No. 7,218,398.

(51) Int. Cl.
*G01J 4/00* (2006.01)

(52) U.S. Cl. ...................................... 356/367
(58) Field of Classification Search ........................ None
See application file for complete search history.

(56) References Cited

U.S. PATENT DOCUMENTS 5,847,799 A * 12/1998 Tanaka et al. ............... 349/174

| | | | |
|---|---|---|---|
| 6,208,403 B1 * | 3/2001 | Tanaka et al. | 349/177 |
| 6,380,997 B1 * | 4/2002 | Sharp et al. | 349/119 |
| 6,473,180 B2 | 10/2002 | Hirosawa | |
| 6,490,036 B2 | 12/2002 | Hirosawa | |
| 7,034,940 B1 | 4/2006 | Hirosawa | |
| 7,218,398 B2 | 5/2007 | Smith | |

FOREIGN PATENT DOCUMENTS

| JP | 2000-241292 | 9/2000 |
|---|---|---|
| JP | 2001-159751 | 6/2001 |
| JP | 2001-165809 | 6/2001 |

(Continued)

OTHER PUBLICATIONS

JP Appln. No. 2008-515919—Jul. 14, 2009 JPO Office Action (English Translation).

(Continued)

*Primary Examiner*—Tu T Nguyen
(74) *Attorney, Agent, or Firm*—Davidson Berquist Jackson & Gowdey LLP

(57) ABSTRACT

Method and apparatus for testing of LCD cells is disclosed. An LCD cell under test (14, 30) may be mounted to translatable table (40) between polarization state generator (10) and polarization state analyzer (16). For each location on cell (14, 30) to be tested, a variety of known polarization states (22) are launched through LCD cell (14, 30) and detected by polarization state analyzer (16). Electrical signals representative of polarization states are acquired by computer (18). Within computer (18), a model (58, 60) of polarization properties of LCD cell (14, 30) is developed based on estimations of what physical parameters of LCD cell (14, 30) are believed to be. RMS differences between simulated polarization properties and measured polarization properties are minimized by iteratively refining (60) modeled physical cell properties, at which point cell thickness and other physical parameters of the LCD cell may be deduced.

28 Claims, 11 Drawing Sheets

FOREIGN PATENT DOCUMENTS

| | | |
|---|---|---|
| JP | 2002-350119 | 12/2002 |
| JP | 2004-80641 | 7/2004 |

OTHER PUBLICATIONS

U.S. Appl. No. 10/998,084, Smith.
U.S. Appl. No. 60/525,407, Smith.
CN Appln. No. 200680028898.7—Aug. 28, 2009 SIPO Office Action (Translation).
CN Appln. No. 200680028898.7—Mar. 1, 2010 SIPO Office Action (Translation).

\* cited by examiner

METHOD AND APPARATUS FOR DETERMINING LIQUID CRYSTAL CELL PARAMETERS FROM FULL MUELLER MATRIX MEASUREMENTS

CROSS REFERENCE TO RELATED APPLICATIONS

This application is a continuation of International Application PCT/US2006/022313 filed Jun. 9, 2006 which designated the U.S. was published under PCT Article 21(2) in English, and claimed priority to U.S. application Ser. No. 11/150,363, filed Jun. 10, 2005, now U.S. Pat. No. 7,218,398.

FIELD OF THE INVENTION

This invention relates generally to apparatus and technique for measuring parameters of a liquid crystal cell, and particularly to apparatus and method for measuring thickness of a liquid crystal layer (cell gap), twist angle that liquid crystal molecules undergo across a thickness of the liquid crystal layer, orientation (rubbing direction) of the liquid crystal molecules at the boundaries of the liquid crystal layer and glass faces of the cell, and tilt angle (pre-tilt) between the liquid crystal molecules and an adjacent glass panel surface.

BACKGROUND OF THE INVENTION

Liquid crystal displays (LCDs) are generally constructed of two glass panels with a thin layer of liquid crystal sealed between them, this assembly known in the art as a "stack". Polarizing films are mounted to both sides of the stack. Transparent electrodes on one of the glass panels of the stack receive a voltage, with the resulting electric field being impressed on adjacent liquid crystal molecules of the liquid crystal material, causing the molecules to change their orientation. This change of orientation of the liquid crystal molecules occurs within a volume of the stack between the electrodes. Where the electrode is relatively large, as in a numeric watch display, a corresponding relatively large volume of liquid crystal material is affected. Where the electrode is tiny, as in pixels of a television screen or computer display, the affected volume of liquid crystal material for each electrode is correspondingly tiny. Because liquid crystal molecules are inherently birefringent, an ability to electrically adjust the liquid crystal molecule orientation at each pixel allows control over the amount of light that passes through the polarizing screens on each side of the stack for that pixel. As is well known in the art, the basis for LCD television and computer screens is an array of a multitude of tiny, transparent electrodes that form pixels, each with electrically adjustable light transmittance characteristics that are adjusted by varying a voltage level applied to respective electrodes. For a large computer display or television, the number of pixels in the LCD screen may run into the millions.

A wide variety of LCD designs are in existence. Referring to FIG. 1, designers can choose the rubbing direction at which the director, or molecular axis, of the liquid crystal molecules orient when at rest, i.e. without application of a voltage to a respective electrode, with respect to the first glass surface. By appropriate selection of the rubbing direction of the second glass surface, twist angle $\Phi$ can be controlled. Referring to FIG. 2, the cell gap, d, which is the space between the glass panels filled with liquid crystal material, and the pre-tilt angle $\Theta$ can also be controlled, where the pre-tilt is the angle between the liquid crystal director and the glass surface. In addition to selecting these cell parameters, designers also select orientation of the polarizers mounted to the outer surfaces of the cell, as well as any birefringent films placed between the liquid crystal cell and the polarizers.

As one example, a common LCD design is the twisted nematic (TN) configuration, in which the twist angle $\Phi$ is chosen to be 90°. A typical TN LCD might have a pre-tilt angle $\Theta$ of 8°, and a cell gap of 5 microns or so. Other designs include the super twisted nematic (STN) mode with twist angles between 180 and 270 degrees, the in-plane switching (IPS) and optically compensated birefringence (OCB) modes with twist angles of 0°, and the vertically aligned nematic (VAN) mode with pre-tilt angles of nearly 90°. Many other modes have also been designed and developed. Each of these designs has its own particular strengths and weaknesses. Some designs have superior field-of-view characteristics, while others have superior switching response times, and others may have the lowest manufacturing costs.

Regardless of the cell or panel design, the ultimate performance of an LCD depends on manufacturing the cell with the correct values of the rubbing direction, twist angle, cell gap, and pre-tilt angle. A variety of techniques and instruments have been introduced for measuring some or all of these parameters. However, these techniques and instruments are often slow, taking something on the order of 20-30 seconds or so to measure a single small location on a liquid crystal cell. As a result, during manufacture, only 5 locations on a cell might be tested, these locations being in the center and generally in each corner region. Such measuring detects cell defects such as misalignments in the rubbing direction, non-uniformity of the cell thickness and other defects.

The instruments for measuring these parameters are critical tools for production and quality control of LCD cells or panels, as well as for research and development. The slow rate of current measuring devices and methods described above obviously limits throughput of cells during manufacture. Existing instruments for measuring these parameters also frequently require several of the parameters to be known a priori and might only provide accurate measurements across a limited range of values. For example, an existing measurement system might require that the rubbing direction of a cell be known in advance, and might only be able to measure pre-tilt angles in the range of 0 to 30 degrees. Another existing measurement system might be unable to differentiate between clockwise and counterclockwise twist sense in the liquid crystal molecules.

Applicant's invention is capable of simultaneously measuring the rubbing direction, twist angle, cell gap, and pre-tilt of any liquid crystal cell. The present invention also has significant advantages over the prior art. As described below, the prior art describes. techniques that only measure a subset of the desired parameters, or that only work for a particular mode of cell, or that require some of the desired parameters to be known in advance, or that require the LC cell to be rotated in order to complete the measurement. The present invention has none of these limitations.

The invention disclosed in U.S. Pat. No. 5,239,365 describes a technique for measuring the thickness of a twisted liquid crystal cell. However this technique requires a priori knowledge of the rubbing direction and twist angle. By aligning linear polarizers in the appropriate direction, this technique can determine the retardance of the cell from spectral transmittance measurements, and then can calculate the cell gap based on the known birefringence An of the liquid crystal material. This technique is lo unable to measure the twist angle or rubbing direction.

The invention disclosed in U.S. Pat. No. 5,532,823 improved on the prior art. By providing spectral transmittance measurements through crossed polarizers, and by allowing continuous rotation of the liquid crystal cell between the polarizers, an approximation method is used to determine twist angle, rubbing direction, and cell gap. This technique requires that the twist angle is less than 120°, and therefore cannot be used to measure STN mode cells.

A further improvement is described in U.S. Pat. No. 6,081,337. In this technique, the liquid crystal cell is not rotated. Instead, polarizers before and after the cell are rotated while spectral transmittance measurements are made. An algorithm is described whereby the appropriate rotation angles for the two polarizers are determined and the rubbing direction, twist angle, and cell gap can be determined.

The three techniques described above each determine the properties of a liquid crystal cell by illuminating the sample with linear polarization states and analyzing the linear polarization component of the light exiting the sample. However, the chiral structure of a twisted liquid crystal cell is such that a significant amount of additional information can be obtained by investigating circular and elliptical polarization states. U.S. Pat. No. 6,300,954 recognized the usefulness of examining the full polarization state (Stokes vector) of light exiting the liquid crystal cell. This technique, however, only launches linear polarization into the cell. The cell is rotated in order to find an orientation that causes a measured maximum or minimum in the transmitted beam. At a located orientation, cell gap and twist angle can be determined from the measured Stokes vector. However, even this recent prior art requires rotation of the liquid crystal cell for measurement, and does not measure rubbing direction.

In the present invention, it is shown that to quickly and accurately measure cell gap, twist angle, and rubbing direction of a liquid crystal cell, it is advantageous to measure the complete Mueller matrix of the cell at one or more wavelengths. It is well known that accurately measuring the Mueller matrix of a sample requires illuminating the sample with a variety of polarization states such as linear, elliptical, and circular, including left-handed and right handed rotations, and analyzing a similar variety of polarization states after they interact with the sample. If the measurements are performed properly, the Mueller matrix of the sample can be measured. The Mueller matrix contains within it all possible polarization-altering properties of the sample, including retarder properties, polarizer properties, and depolarization properties. Prior to the present invention, there have been only a few papers that describe the theoretical or measured Mueller matrices of a liquid crystal cell.

The description in "J. Opt. Soc. Am." (Vol. 68, pages 1756-1767, 1979) teaches a way to mathematically derive the Mueller matrix for a twisted nematic liquid crystal cell. However, no further analysis is provided, and no experimental results are shown. In "Appl. Opt." (Vol. 37, pages 937-945, 1998), the mathematical derivations of the Mueller matrix of twisted nematic liquid crystal cell are furthered by calculating the polarization eigenstates of the theoretical Mueller matrices. However, no measurements are presented, and the purpose of this work was to find the polarization eigenstates of twisted nematic liquid crystal cells so that the devices could be used to achieve phase-only modulation for use, presumably, in optical correlation or other optical computing applications. That theoretical work actually followed the experimental measurements described in "Opt. Lett." (Vol. 18, pages 1567-1569, 1993), which is the only reference we are aware of that shows the measured polarization eigenstates of a twisted nematic liquid crystal device. These measurements were made at a single wavelength, and were made as a function of applied voltage to the liquid crystal. The purpose of this work was to find these eigenstates so that the device could be used as a phase-only modulator for optical correlation applications. Finally, in "Meas. Sci. Technol." (Vol. 12, pages 1938-1948, 2001), we find the only other set of Mueller matrix measurements on liquid crystal cells that we are aware of. In that article, investigations of crystal asymmetries and switching response times of ferroelectric liquid crystal cells are made using Mueller matrix measurements.

To summarize our survey of the prior are, it is seen that the prior art can be separated into two categories: patents that describe methods and apparatuses for measuring the physical properties of liquid crystal cells, and academic research papers that theoretically model or experimentally measure the Mueller matrix of liquid crystal cells. The patented techniques have been evolving from simple systems that were limited in their capability toward more complex systems that can measure more polarization properties, and thus, more parameters of the liquid crystal cell. However, no patented technique has yet advocated the level of, system complexity required for complete polarization characterization, that is, the full Mueller matrix measurement. The academic research papers have either derived what the Mueller matrix for liquid crystals should be, or have measured the Mueller matrix of liquid crystal cells with analysis for various research purposes. The purpose of these papers has always been to investigate the optical properties of LC cells. These papers have not considered inverting the problem, that is, using the measured optical properties to go back and determine the physical properties of the cell. None of these papers have presented experimental measurements or theoretical analysis that advocates the use of full Mueller matrix measurements for simultaneously and uniquely determining the rubbing direction, twist angle, cell gap, and pre-tilt of liquid crystal cells.

It is, therefore, one object of the present invention to provide a measurement method of the Mueller matrix of liquid crystal cells wherein one or more of the parameters comprising cell gap, twist angle, and rubbing direction can be determined exactly even if their values are previously unknown.

Another object of the present invention is to provide a measuring apparatus for measuring the optical properties of liquid crystal cells, even if the cell gap, twist angle and rubbing direction of the cell are previously unknown, and which does not require the liquid crystal cell to be rotated during the measurement.

Another object of the present invention is a method of manufacturing liquid crystal devices with desired values of cell gap, twist angle, and rubbing direction.

Another object of the present invention is to provide a measurement method of the Mueller matrix of liquid crystal cells where the pre-tilt of the liquid crystal directors is determined by varying the incident angle of the measurement beam on the liquid crystal device, and where the pre-tilt angle can be any value from 0 to 90 degrees.

Another object of the present invention is a measuring apparatus for measuring the pre-tilt of the liquid crystal directors of a liquid crystal cell, where the pre-tilt angle can be any angle from 0 to 90 degrees.

Another object of the present invention is a method of manufacturing liquid crystal devices with a desired value of the pre-tilt angle.

Further objects of the invention will become apparent upon a reading of the following appended specifiction

BRIEF DESCRIPTION OF THE DRAWINGS

FIG. 6a shows the so-called 'splay' state and FIG. 6b shows the 'bend' state.

DETAILED DESCRIPTION OF PREFERRED EMBODIMENTS

To measure a Mueller matrix of a liquid crystal cell, light formed into a variety of different polarization states is directed into the liquid crystal cell, the cell altering these polarization states in accordance with the cell's properties. A polarization-sensitive detection system analyzes polarization states emerging from the cell. In order to accurately measure the Mueller matrix, the generated light input containing the variety of polarization states and measured polarization states must both sample a large portion of the Poincaré sphere. That is, a variety of polarization states with significantly different orientation, ellipticity, and handedness must be generated and analyzed. Once the Mueller matrix of the liquid crystal cell has been measured, the cell gap, twist angle, and rubbing direction are determined. If all three parameters are previously unknown, then Mueller matrix measurements at multiple wavelengths are required, and these parameters are iteratively varied in a computer simulation of the cell until the simulation and measurements match as closely as possible. In other cases where, for example, the values of twist angle and rubbing direction are known a priori, a Mueller matrix measurement at a single wavelength is sufficient for determination of cell gap.

The measurements described above typically require that the birefringence Δn and the pre-tilt angle Θ are known prior to the measurement, as is most often the case. In cases where the pre-tilt is not exactly known, it is advantageous to be able to measure the pre-tilt angle.

To measure the pre-tilt angle, the same Mueller matrix measurement technique described above is used, in addition to a mechanical fixture that allows the input direction and incident angle of the measurement beam to be varied. By measuring the Mueller matrix as a function of incident angle, and by comparing these measured results to either analytical expressions or computer simulations, the pre-tilt angle of the liquid crystal can be determined.

Figure 3:
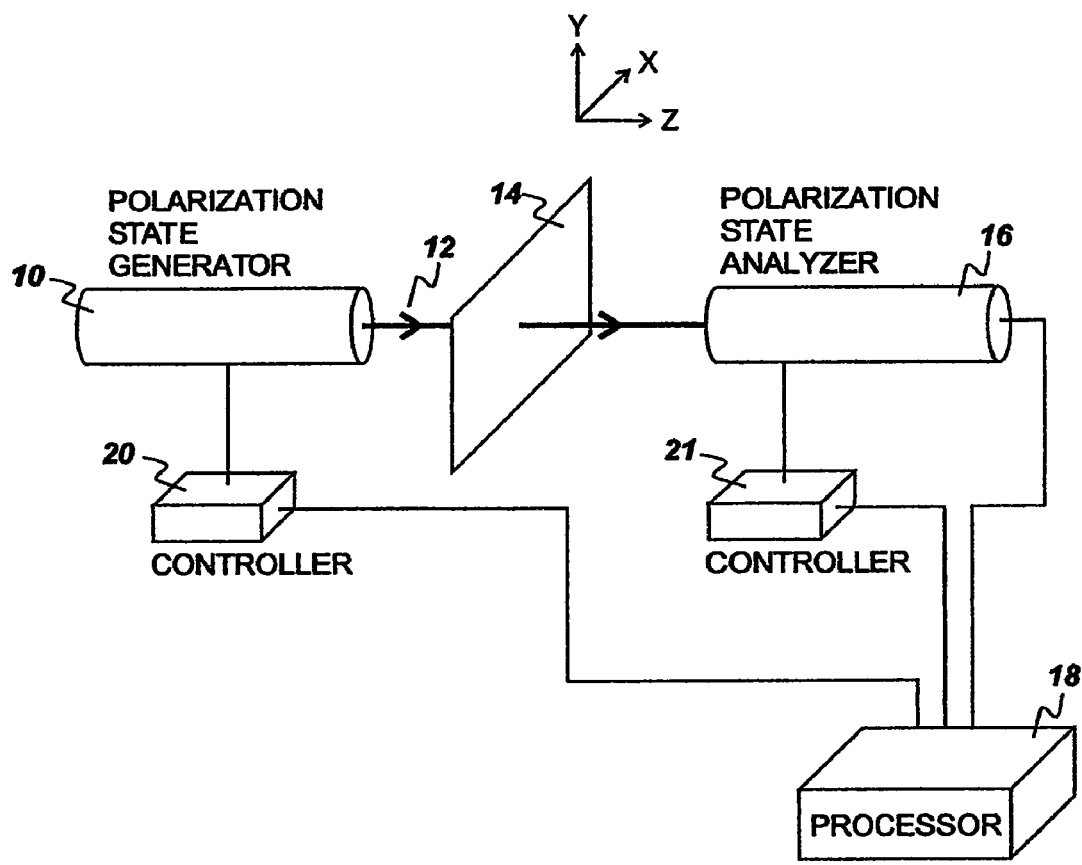
FIG. 3 is a block diagram showing the necessary components for measuring the Mueller matrix of a liquid crystal cell.

FIG. 3 illustrates basic elements of the current invention. A polarization state generator 10 creates an optical beam 12 having time-varying polarization states. This beam interacts with sample 14, in this case an LCD cell, causing some or all of the polarization states of beam 12 to be altered. The altered polarization states are analyzed by a polarization state analyzer 16. Polarization state analyzer 16 measures a time-varying sequence of polarization states, or simultaneously may measure a discrete number of fixed polarization states by dividing the beam and passing the divided beams each through a different, respective fixed polarization element and detector. The polarization state generator and polarization state analyzer are each controlled by a processor 18, such as a micro-controller or personal computer. Processor 18 calculates a Mueller matrix (FIG. 8) of the sample based on known polarization states launched by polarization state generator 10 and measured values from polarization state analyzer 16. Once the Mueller matrix has been measured, processor 18 calculates desired parameters of liquid crystal cell 14, such as cell gap, twist angle, rubbing direction, and pre-tilt angle to determine as early as possible during the manufacturing process those LCD cells that are defective. It is emphasized that Applicant's invention will quickly allow determination of the stated parameters in less than a second or so for each location on the LCD cell tested, as opposed to the 20-30 seconds or so currently required by methods of the current state of the art. Such tests are related generally to color purity of the finished LCD viewing screen. For example, where the cell gap of nominally five microns varies outside factory specifications, the area of variance will produce, on a white or black colored screen, a predominantly lighter or darker shaded area. On a television or computer screen, such an area may have a predominant, undesired color tint associated with the area that is out of tolerance. Thus, it is important to identify such defective cells early in the manufacturing process so that the cell may be discarded or recycled. Further tests on the LCD cells are performed later in the manufacturing process, such as electrical tests to determine a number of possible dead pixels. Controllers 20, 21 control the rotation rate of state generator 10 and state analyzer 16, as described in my referenced application.

Figure 4:
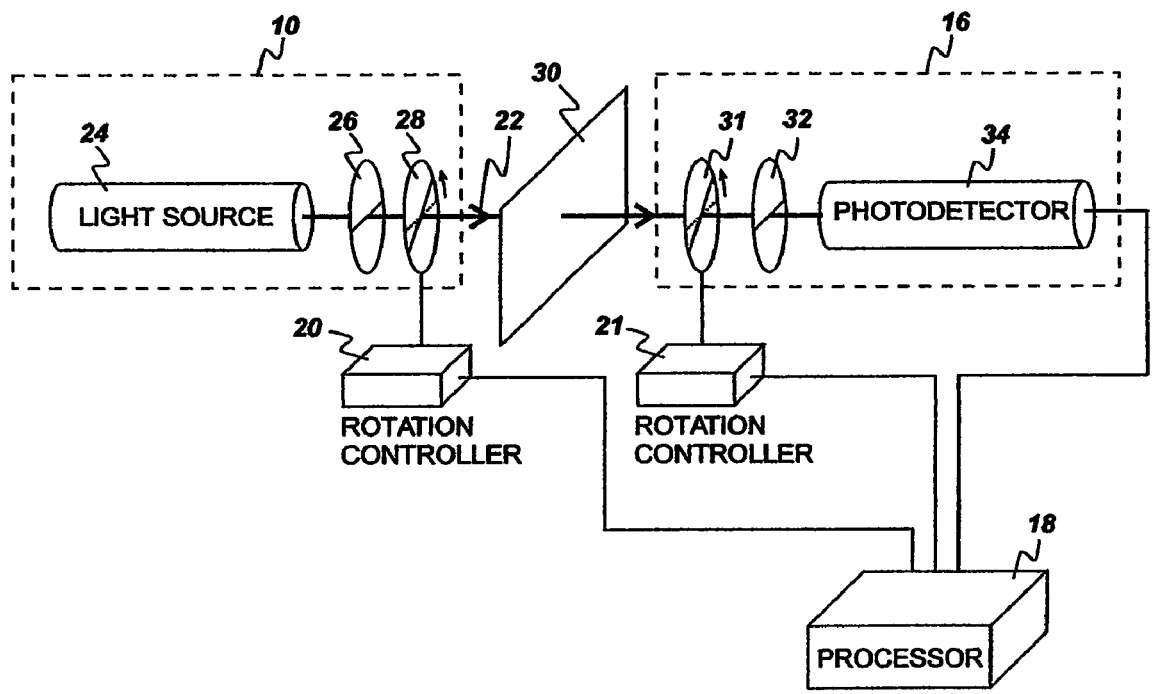
FIG. 4 is a block diagram of one implementation of the Mueller matrix measurement system expanding on the block diagram shown in FIG. 3.

FIG. 4 illustrates one possible embodiment of a Mueller matrix measurement system of my invention as described fully in my patent application entitled "Complete Polarimeter" as referenced above, the apparatus of which may be appropriately scaled and used to obtain measurements of an LCD cell. One contemplated modification to the apparatus of the referenced application would be to enlarge an X-Y translatable table in order to receive an LCD cell for sampling. In the instant application, the polarization state generator of FIG. 3 is shown as providing a collimated optical beam 22 generated by a light source 24, the light beam directed through a horizontal linear polarizer 26 and then through a continuously-rotating retarder 28 with approximately one-third wave of retardance. As described in my referenced application, this results in a continuuum of time-varying polarization states projected through sample 30, i.e. the LCD cell mounted to an appropriately sized X-Y translatable table so that the cell may be moved in order to measure various locations of the cell. The polarization state analyzer 16 of FIG. 3 may be constructed having a continuously-rotating retarder 31 with approximately one-third wave of retardance, followed by a horizontal linear polarizer 32, followed by a photodetector 34. The two rotating retarders 28, 31 are rotating at a non-whole integer ratio that approximates 5:1, and the processor calculates the Mueller matrix of the cell.

Figure 5:
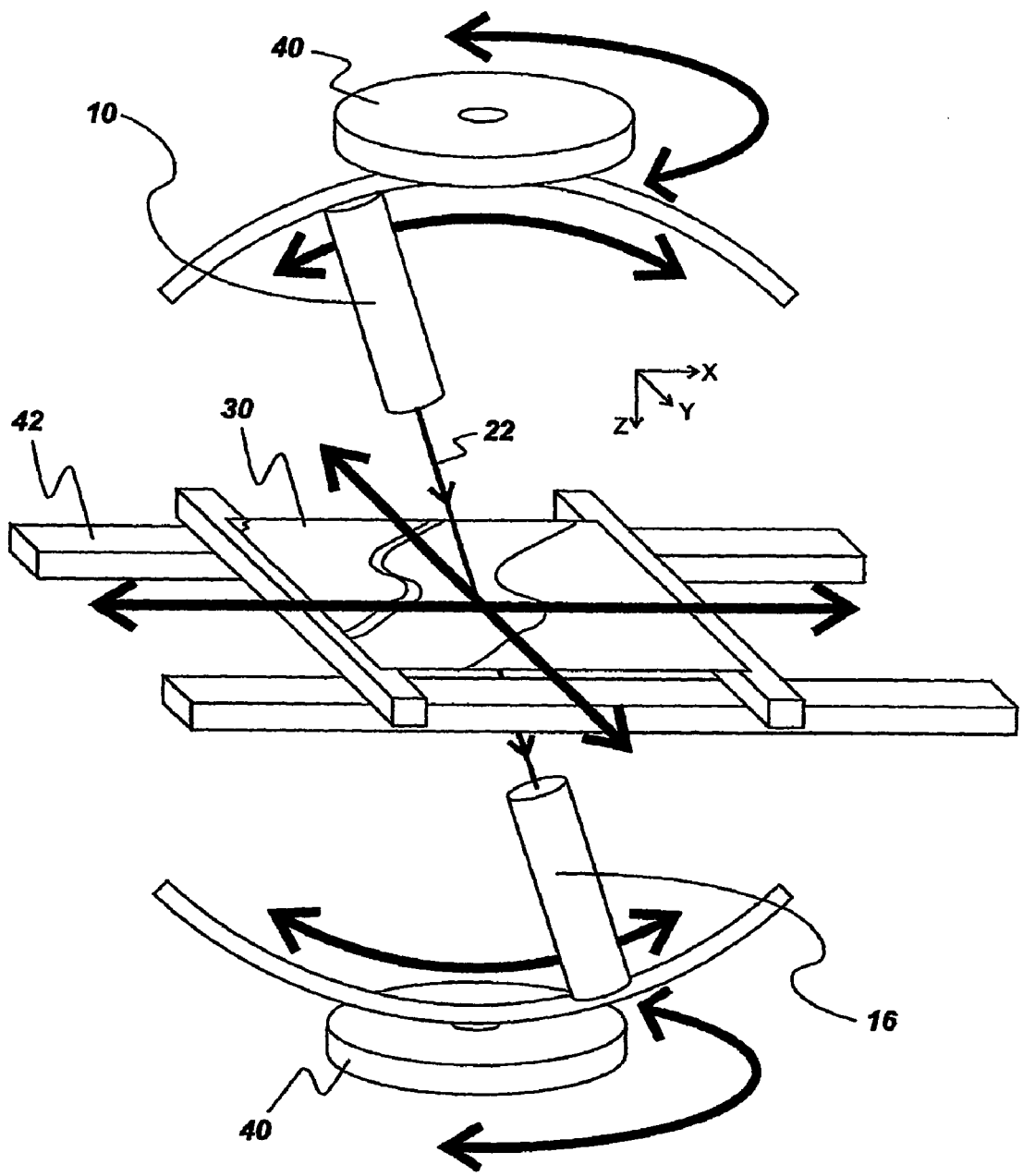
FIG. 5 is a diagrammatic view of a mechanical fixture whereby robotic actuators translate an LCD device in the XY plane between the polarization state generator and the polarization state analyzer for mapping out spatial variations in liquid crystal parameters. Additionally, the polarization state generator and the polarization state analyzer are mounted on fixtures that can be tilted and rotated to achieve an arbitrary incident direction and angle, allowing measurement of the pre-tilt angle of the liquid crystal.

FIG. 5 illustrates diagrammatically the system shown in my referenced application wherein my polarization state generator 10 and polarization state analyzer 16 are mounted within a robotic control system 40 that maintains alignment of generator 10 and analyzer 40 while allowing an angle of incidence of collimated light beam 22 to be varied up to about 80 degrees or so. This is facilitated by the robotic control system to which generator 10 and analyzer 16 are mounted being a 2 axis system so that beam 22 may be directed in any angular direction through cell 30. In addition, robotic controller 40 includes linear translators 42 that move cell 30 in directions so that multiple locations on cell 30 may be tested.

The current invention incorporates an additional step of measuring a particular set of Mueller matrices and using this data to calculate desired parameters of liquid crystal cell 30, such as cell gap, twist angle, rubbing direction, and pre-tilt angle. Choosing which set of Mueller matrices to measure depends on which of the liquid crystal parameters are known a priori, and which are to be measured. For example, the pre-tilt angle is often known, and in this case measuring the Mueller matrix at normal incidence at one or more wavelengths provides sufficient data for calculating the cell gap, twist angle, and rubbing direction. As another example, often the twist angle is known to be zero. In this case, the pre-tilt and cell gap can be determined by measuring the Mueller matrix as a function of incident angle where the incident plane is chosen to be along or perpendicular to the liquid crystal director. In cases where no information about the liquid crystal cell is known, the Mueller matrix can be measured at one or more wavelengths and at one or more incident angles in order to determine all of the cell parameters. In all cases, the technique for calculating the liquid crystal cell parameters from the measured Mueller matrices is the same, and is as described below.

To determine the parameters of a liquid crystal cell, the measured Mueller matrices are compared to a mathematical model (computer simulation) of the cell, where the model has the free parameters of the rubbing direction, twist angle, cell gap, and pre-tilt angle. Typically, birefringence $\Delta n$ of the liquid crystal material is already known as a function of wavelength. It is possible that the birefringence is only known at one wavelength and that the wavelength dispersion is also a free parameter in the model.

To create this mathematical model, the liquid crystal cell is modeled as Q individual homogeneous layers of uniaxial birefringent material, where Q is a large number such as 50. For liquid crystal cells with a large twist angle or in other instances where necessary or desired, a larger number of layers, for example 400 or so, may be used or required for increased accuracy of the simulation. Each birefringence layer is modeled as, a uniaxial material with known values of $n_e$ and $n_o$, the ordinary and extraordinary refractive indices, respectively. The extraordinary axis of the refractive index ellipsoid is aligned along. the directors of the liquid crystal molecules for each individual layer. For layer 1 and layer Q that are in contact with the glass panels of the cell, the director is tilted with respect to normal by the pre-tilt angle of the cell. For layer 1, the director orientation in the xy plane is given by the rubbing direction. For layer Q, the director orientation in the xy plane is given by the rubbing direction of layer 1 plus the twist angle. For the layers 2 through Q-1, the tilt angle and orientation are modeled to vary linearly from layer 1 to layer Q, which is a valid assumption when there is no voltage applied to the liquid crystal cell as this approximated the lowest free-energy configuration, or resting state of the liquid crystal molecules. In yet other instances where higher accuracy of the mathematical model is desired or required, the linear variation in tilt angle and orientation can be replaced with the results of a mechanical simulation that varies in a known manner, such as the elastic coefficients of the liquid crystal molecules. Such a simulation would take into account non-linear aspects of a simulated liquid crystal material. The Elastic Continuum Theory is based on such means of determining the lowest free-energy configuration of the liquid crystal molecules. Using the Elastic Continuum Theory model will increase the simulation accuracy, but will also increase the computation time required.

Figure 1:
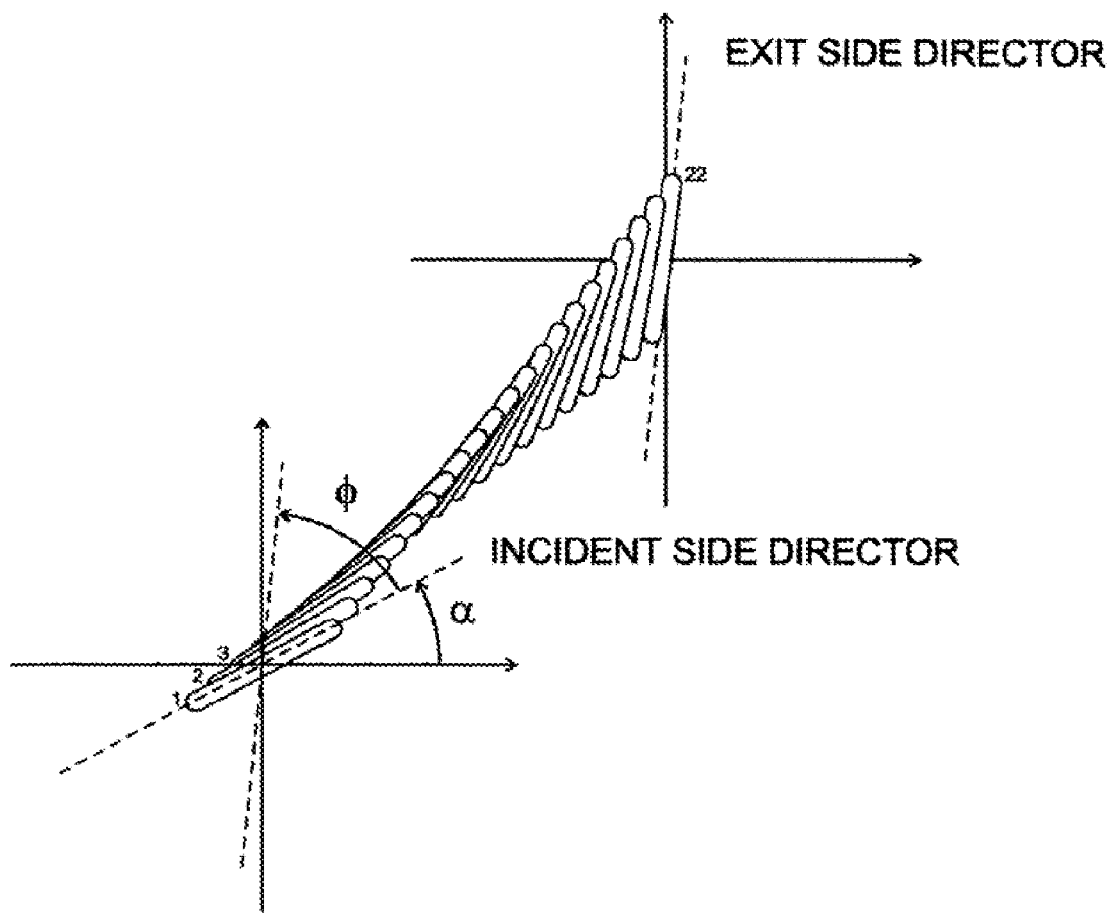
FIG. 1 is a 3D diagrammatic illustration of liquid crystal molecules in a twisted arrangement. The molecular directors align with the rubbing direction α at the input (incident) glass, and twist uniformly by twist angle Φ when they reach the exit side.
Figure 2:
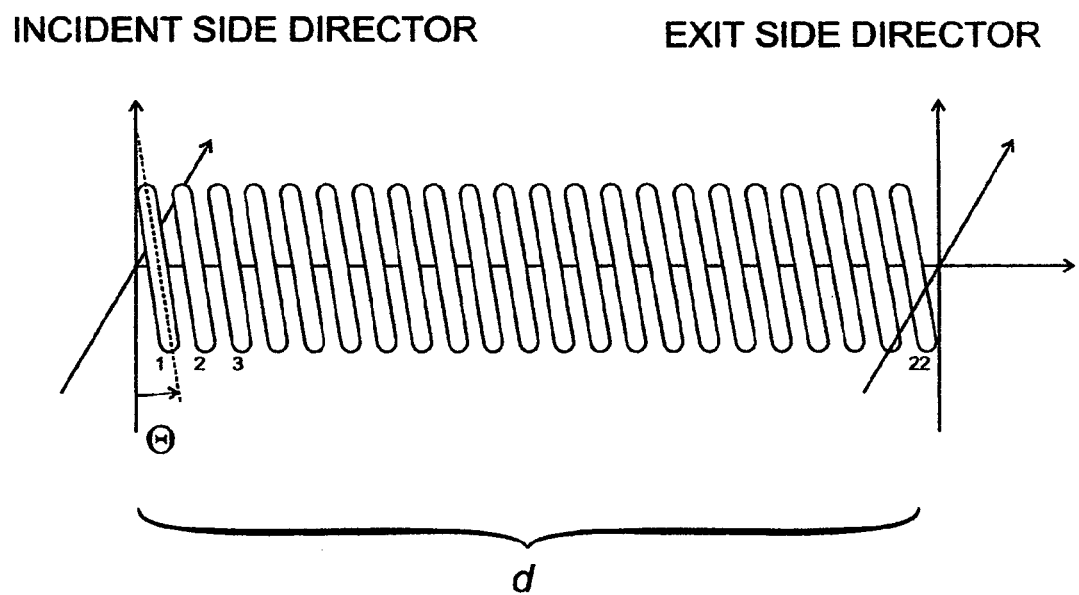
FIG. 2 depicts a diagrammatic side view of the liquid crystal directors with no twist from the input (incident) side to the exit side. Here, the cell gap is given by d and the pre-tilt angle of the directors is given by Θ.
Figure 6A:
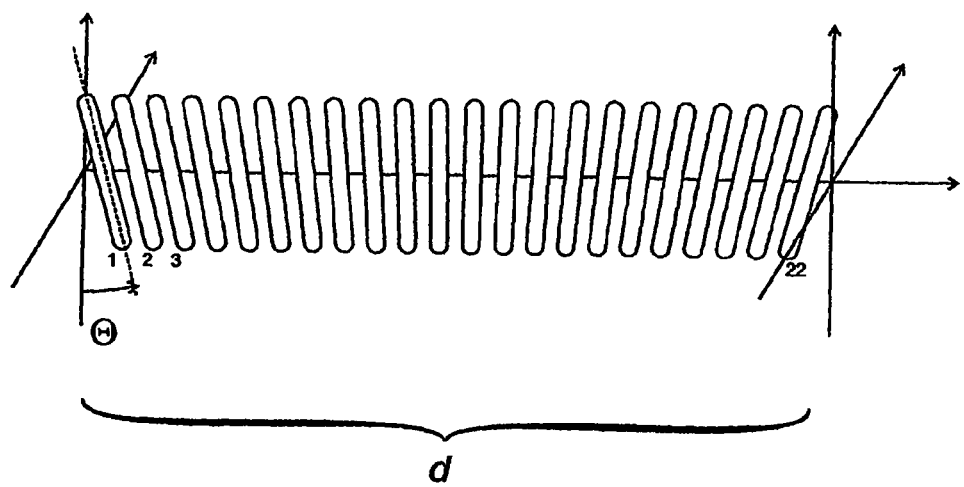
FIGS. 6a and 6b are diagrammatic illustrations of two cells that both have the same pre-tilt and both have zero twist angle.
Figure 6B:
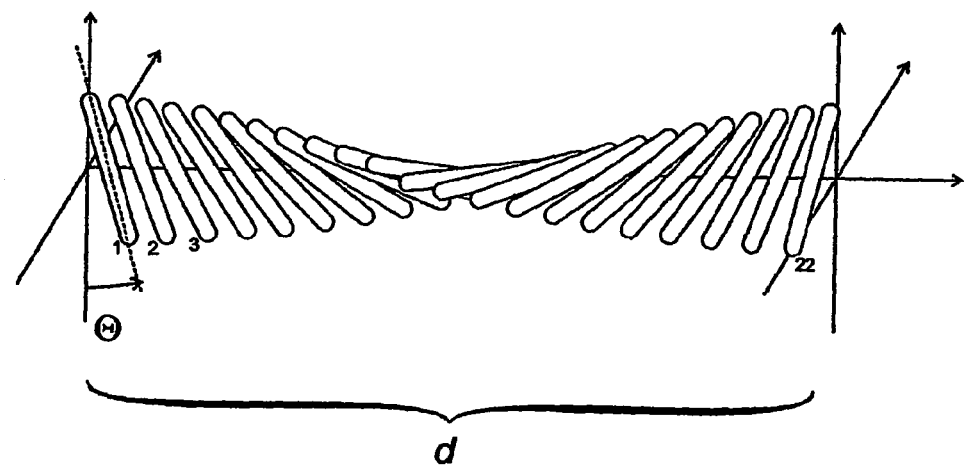

To illustrate this model, refer to FIGS. 1, 6a and 6b. In FIG. 1, we see the case where 22 layers are shown, designated 1-22 (Q=22), the pre-tilt is zero, the director orientation at layer 1 is $\alpha$, and the orientation varies linearly to angle $\alpha+\phi$ at layer Q. In FIG. 6, we see two cases where Q=22, the orientation at layer 1 and layer Q are the same angle $\Theta$, and the twist angle is zero. The top illustration in FIG. 6 shows the 'splay' mode for this cell, and the bottom illustration in FIG. 6 shows the 'bend' mode for this cell. The difference between these modes is whether the tilt angle is allowed to linearly increase or linearly decrease through the cell. Both modes are physically realizable by the liquid crystal cell manufacturer, and either mode can be modeled.

To implement this model, the Mueller matrix of each layer is calculated based on the known optical wavelength, the known propagation direction of the light, the known birefringence of the liquid crystal material, and the presumed values of the pre-tilt, rubbing direction, cell gap, and twist angle. Once the Q individual Mueller matrices are calculated, the total Mueller matrix of the cell is calculated as $$M_{cell} = M_Q \cdot M_{Q-1} \ldots M_2 \cdot M_1$$

where $M_{cell}$ is then calculated for each optical wavelength or incident direction in the measured dataset. The presumed values of the pre-tilt, rubbing direction, cell gap, and twist angle are then iteratively modified until the modeled Mueller matrices match the measured Mueller matrices with the lowest achievable RMS difference between modeled and measured points. As is well-known to those skilled in the art, any standard optimization algorithm such as the Gauss-Newton Method, Gradient Descent Method, or the Levenberg-Marquardt Algorithm, is suitable for this purpose.

Figure 7:
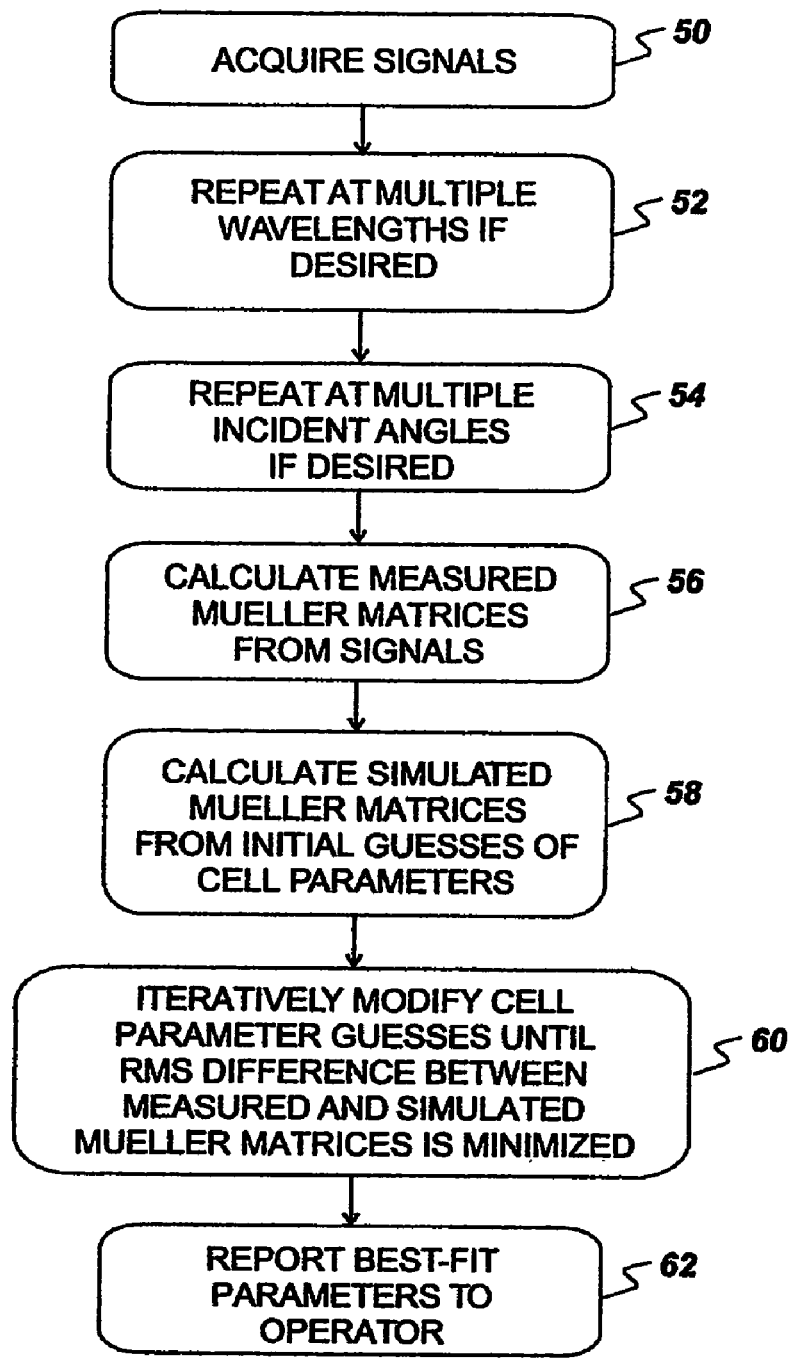
FIG. 7 is a flow chart illustrating one possible process for measuring parameters of a liquid crystal cell.

FIG. 7 is a flow chart of the processes required to determine the liquid crystal cell parameters. Here, at box 50 light source 24 is energized and rotation of retarders 28, 31 begun. Signals are acquired from photodetector 34 by computer 18 for processing.

At box 52 samples may be taken at multiple wavelengths if necessary. Generating data at multiple wavelengths can be achieved in several ways. For example, light source 24 could be a white light source such as a halogen bulb or arc lamp followed by a motorized filter wheel containing a plurality of narrow band interference filters. These spectral filters can be individually selected by issuing commands to the filter wheel from processor 18 via an RS-232 port, typically under control of a computer or controller. Alternately, light source 24 could consist of a white light source followed by a monochromator that would allow any wavelength to be selected by issuing commands from processor 18. Alternately, light source 24 could consist of a white light source and the photodetector 34 could consist of a spectrometer.

At box 54 multiple incidence angles may be selected for sampling. These incident angles are generated by processor 18 sending appropriate commands to the robot fixtures 40.

At box 56 the measured Mueller matrices are calculated. One measured Mueller matrix is determined for each wavelength and incident angle setting. These are the Mueller matrices that describe the cell being measured.

At box 58, a computer simulation is performed that calculates the simulated Mueller matrices based on initial estimations for the cell gap, twist angle, rubbing direction, and pre-tilt. One simulated Mueller matrix is calculated for each measured wavelength and incident angle, that is, each measured Mueller matrix from the sample will have one corresponding simulated Mueller matrix. At box 60, the initial guess values of one or more of the cell gap, twist angle, rubbing direction, and pre-tilt are iteratively varied. At each iteration, new simulated Mueller matrices are calculated and then compared to the measured Mueller matrices. The RMS difference between the elements of the simulated and measured Mueller matrices is used as a figure-of-merit in the optimization procedure. The cell parameters that are estimated in the simulated Mueller matrices are iteratively changed until the RMS difference is minimized, or until the RMS difference reaches a sufficiently low value, generally indicating a close match with the LCD cell under test. Techniques for. choosing the iteration step sizes and for maximizing a rate at which the optimization process converges to a solution are well-known to those skilled in the art. For example, the Gauss-Newton Method, Gradient Descent Method, and Levenberg-Marquardt Algorithm are all suitable for this purpose. Once the optimized values for the cell gap, twist angle, rubbing direction, and pre-tilt are known, the values are reported to the user at box 62.

When matching the modeled data to the measured Mueller matrices, it is advantageous to match the values in the lower 3×3 sub-matrix of the normalized Mueller matrices. Using the normalized Mueller matrix removes the effects of the color filter or other spectral properties of the cell from the calculations. The lower 3×3 sub-matrix contains the retardance information of the Mueller matrices, and liquid crystal devices are typically retardance-only devices. At incidence angles other than 0°, the differences between the s- and p-reflectances of the glass cells will introduce some diattenuation, that is, the cell will also act as a partial polarizer. In this case, it is advantageous to perform a polar decomposition of the Mueller matrices and perform the curve-fit on only the pure-retardance Mueller matrix.

Figure 8:
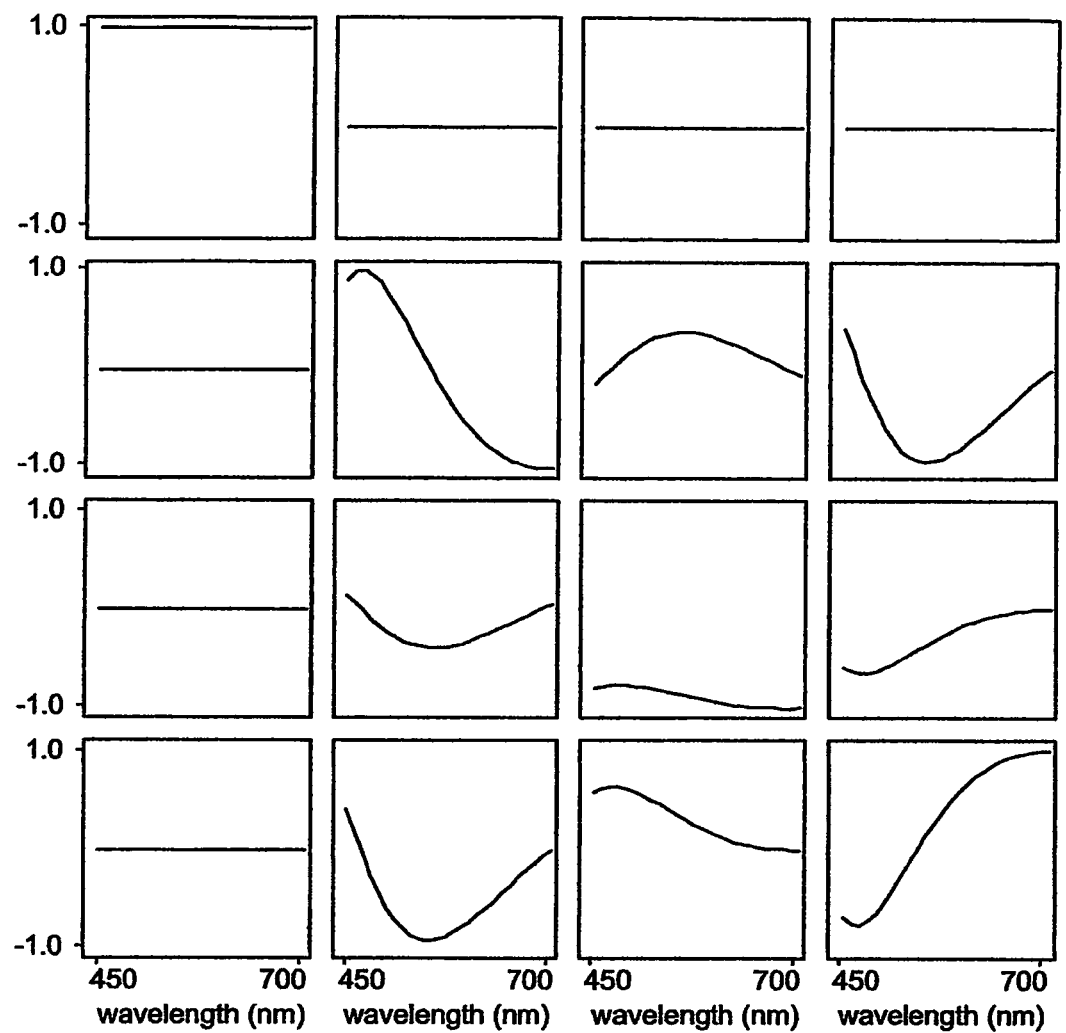
FIG. 8 shows a normalized Mueller matrix of a twisted nematic liquid crystal cell. Each of the 16 matrix elements has been plotted as a function of wavelength.

FIG. 8 graphically illustrates the components of the normalized Mueller matrix for a twist-nematic type of liquid crystal cell. The elements of the Mueller matrix vary smoothly as a function of wavelength. Even for the most general case, where the retardance order crosses multiple orders, the Mueller matrix elements will behave smoothly and not have discontinuities, making the Mueller matrix elements most suitable for curve-fitting.

Figure 9A:
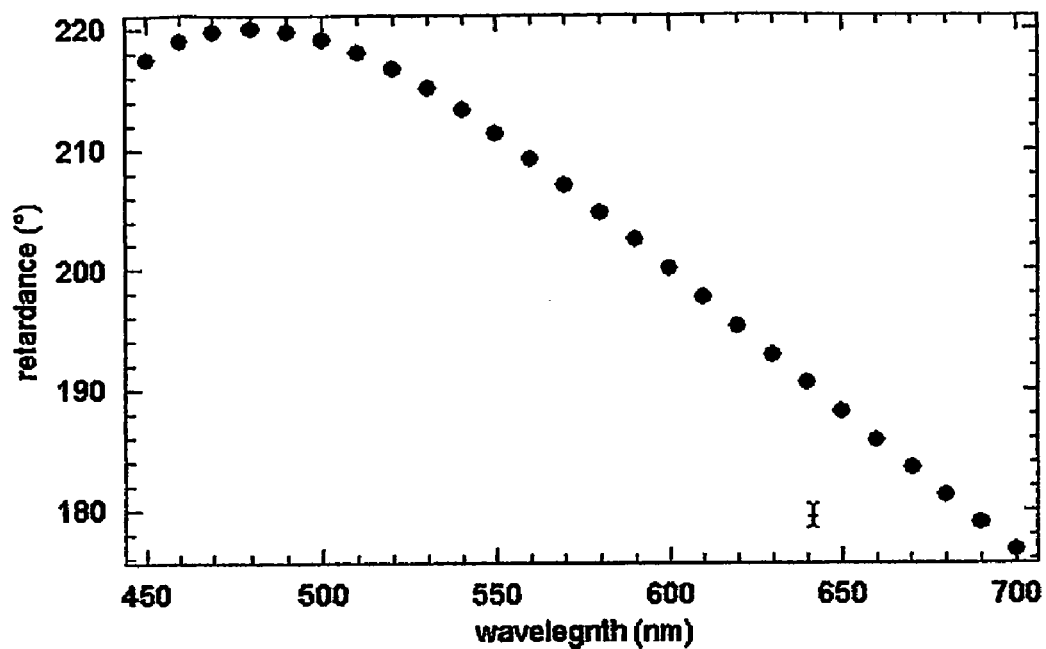
FIGS. 9a and 9b shows the retardance and fast-axis (eigenpolarization) of the twisted nematic liquid crystal cell shown in FIG. 8 as a trajectory on a Poincaré sphere.
Figure 9B:
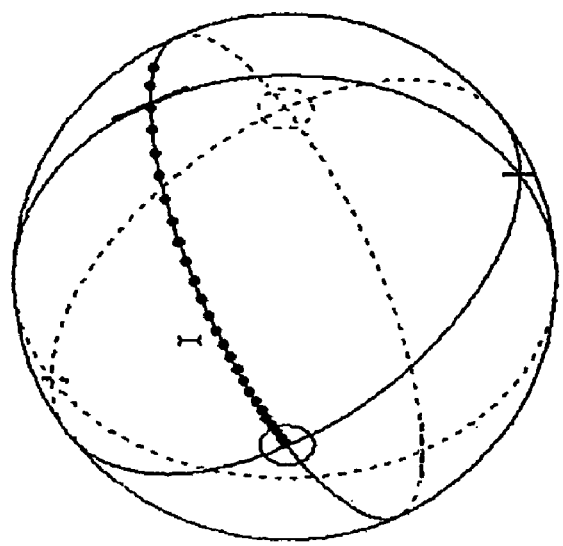

FIGS. 9a and 9b show the same data as shown in FIG. 8, however FIG. 9a shows retardance magnitude, with FIG. 9b showing retardance fast-axis that have been calculated via an eigenanalysis of the Mueller matrix data in FIG. 8. It is well-known to those skilled in the art that the calculated retardance and fast-axis will have discontinuities every time the retardance magnitude exceeds an additional 180° of retardance. It becomes necessary to determine the true 'order' of the retardance at each point and apply an algorithm that attempts to unwrap the magnitudes and fast-axes so that the plots are continuous. In fact, the data in FIGS. 9a and 9b has already been unwrapped as can be seen by the retardance exceeding 180° at wavelengths of 680 nm and lower. While FIGS. 9a and 9b are very useful in helping to understand and visualize the behavior of the liquid crystal device, it is less useful for the actual act of curve-fitting.

Figure 10:
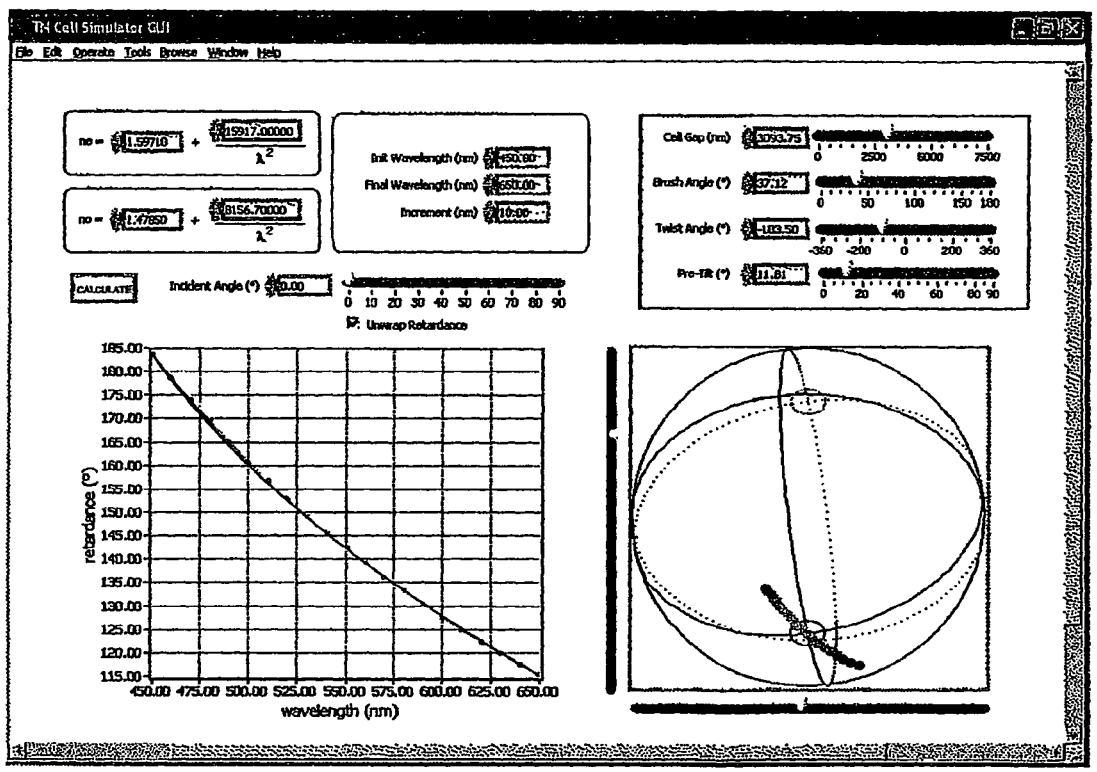
FIG. 10 shows an example of a graphical user interface that may be used in a research and development environment.

FIG. 10 illustrates by way of example one possible graphical user interface that a researcher might use in a research and development environment to control the present invention and to interpret the resulting data. Here, the researcher is presented with graphical representations of the Poincaré sphere and retardance versus wavelength. The various cell parameters can be individually manipulated by sliders for cell gap, brush angle, twist angle, pre-tilt and incident angle. In addition, vertical and, horizontal sliders allow manipulation of the Poincaré sphere to allow it to be viewed from a convenient orientation. Such manipulation of cell parameters is useful for comparing the simulated polarization properties to the measured polarization properties. In addition, a CALCULATE button can be pressed to begin the optimization routine that determines the best-fit cell parameters based on the measured Mueller matrix data.

Figure 11:
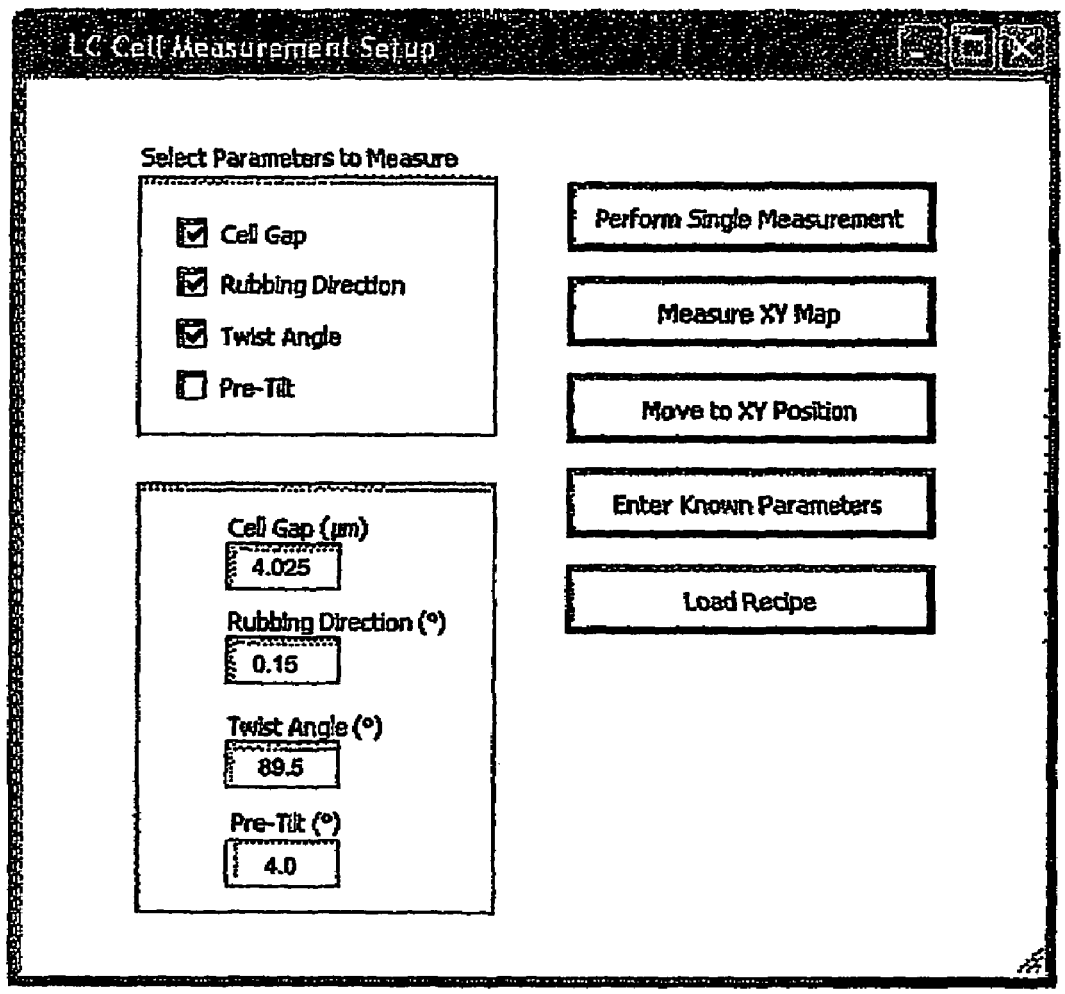
FIG. 11 shows an example of a graphical user interface that may be used in a production environment.

In a manufacturing environment where technicians or other workers will be repeatedly making the same measurement on multiple cells in an assembly line manner, a simplified interface such as the one shown in FIG. 11 may be likely preferable. Here, complete measurements can be performed with a single button click of a pointing device or touch on a touch screen or the like. Pressing the "Perform Single Measurement" button would automatically measure and display the values of cell gap, rubbing direction, twist angle, and pre-tilt. This measurement might be based on a "recipe" that was previously defined. Such a recipe might indicate what tilt angles, optical wavelengths, and cell locations are to be measured, and might specify a database into which measured parameters are stored. When one or more of the cell parameters are known a prioni, and therefore do not need to be measured, those parameters can be entered and can then be excluded from the optimization routine. It is emphasized that where none of the parameters are known a priori, the system can be programmed to measure at sufficient wavelengths and incident angles in order to be able to calculate all of the parameters. The interface might also include a button that lets the operator measure a specific XY location on the cell, or to perform an automated XY map measurement.

It should be noted that throughout this application, I have described a technique where the physical parameters of a liquid crystal cell are determined by the following steps: A series of different polarization states are directed through a liquid crystal cell, the altered polarization states then pass through a polarization state analyzer, the optical power in each analyzed polarization state is measured with a photodetector, the Mueller matrix of the liquid crystal. cell is calculated from the measured optical powers and the known polarization states that were generated and analyzed, the Mueller matrix measurement is made at one or more optical wavelengths and one or more incident beam directions, a computer simulation of the Mueller matrix of the liquid crystal cell is developed for the same optical wavelengths and incident beam directions, the parameters of the computer simulation are iteratively varied until the RMS difference between the simulated Mueller matrices and the measured Mueller matrices are minimized, and the resulting final parameters of the computer simulation described the true parameters (cell gap, rubbing direction, twist angle, pre-tilt angle) of the liquid crystal cell. It should be apparent to those skilled in the art that these steps can be slightly modified or regrouped and still fall within the scope of the current invention. For example, it is possible to realize exactly the same result by removing the step of converting the measured optical powers into a Mueller matrix, and adding a further step to the computer simulation that simulates the optical powers that would be measured by the photodetector, and then iteratively varying the parameters of the computer simulation to minimize the RMS difference between the simulated optical powers and the measured optical powers, instead of directly comparing the Mueller matrices. Alternately, one might choose to minimize the peak difference instead of the RMS difference between the Muelles matrices to achieve a similar result.

It should also be noted that throughout this application, I have talked about the Mueller matrix of the sample cell. Everything that has been described is equally valid for a system that measures the Jones matrix of a sample. For samples that exhibit no depolarization effects, there is a one-to-one relationship between the Mueller matrix and the Jones matrix (less an absolute phase term that can be arbitrarily multiplied into the Jones matrix). In general, the Mueller matrix is more advantageous for experimental work since it can also include depolarization effects and it does not have the undetermined absolute phase term present in the Jones matrix. Nevertheless, a technique that used the measured Jones matrix instead of the Mueller matrix would be another embodiment of the current invention.

Finally, it should be noted that there are several slight variations to the liquid crystal computer simulation that could be made that would fall within the scope of the current invention. When calculating the Mueller matrix of the liquid crystal cell at incident angles that are not zero, the partial polarizing effect of the glass plates of the liquid crystal cell can be modeled based on the Fresnel reflection coefficients, and these simulated Mueller matrices are then c compared to the Measured Mueller matrices as described above. This will give the same results; as previously described where the model ignores the Fresnel reflection coefficients at non-zero incident angles and a polar decomposition of the measured Mueller matrices is performed so that the pure-retardance portion of the measure Mueller matrices are compared to the simulated Mueller matrices.

With computers currently in use today with speeds greater than 3 GHz, 64-bit processors, dual-core processors and the like, calculation of the Mueller matrix for determining parameters related to LCD cells and comparing of these calculated parameters to a computer model is exceedingly fast. Calculating in excess of 5,000 simulated LCD Mueller matrices per second can be reasonably achieved. As described, such modeling and calculations may be accomplished in less than one second or so, reducing testing time from 2-3 minutes or so per cell down to a few seconds, greatly increasing throughput of the testing process.

Having thus described my invention and the manner of its use, it should be apparent to those skilled in the appropriate arts that incidental changes may be made thereto that fairly fall within the scope of the following appended claims, wherein

I claim:

1. A liquid crystal viewing screen tested for defects during manufacture according to a method utilizing a computer processor for determining at least one physical parameter of a liquid crystal cell under test to determine whether said liquid crystal cell under test is defective comprising:

A) directing sequences of polarization states generated by a polarization state generator at said liquid crystal cell under test, each polarization state of said sequences of polarization states differing from other polarization states of said sequences of polarization states in orientation, ellipticity and handedness, B) analyzing said sequences of polarization states as modified by said liquid crystal cell under test by a polarization state analyzer, and converting analyzed said sequences of polarization states into corresponding sequences of electrical signals, C) using said computer processor to calculate polarization properties of said liquid crystal cell under test from said sequences of electrical signals, D) using said computer to develop a computer model including at least one estimated physical parameter of said liquid crystal cell under test, and adjust said at least one estimated physical parameter until a close match is obtained between analyzed said polarization properties of said liquid crystal cell under test and calculated said polarization properties of said computer model of a liquid crystal cell, E) providing at least one indication of a closely matched said estimated physical parameter representative of a corresponding physical parameter of said liquid crystal cell under test, wherein said at least one indication further comprises indicating one or more of the group of said estimated physical parameters comprising cell gap, twist angle, rubbing direction and pre-tilt angle.

2. A liquid crystal viewing screen tested for defects during manufacture according to the method set forth in claim 1 further comprising:

calculating a polarization matrix of said liquid crystal cell under test, said polarization matrix indicative of polarization properties obtained from analyzed said sequences of polarization states as modified by said liquid crystal cell under test, calculating a polarization matrix indicative of polarization properties of said computer model of said liquid crystal cell under test, iteratively modifying one or more of said estimated physical parameters comprising pre-tilt, rubbing direction, cell gap and twist angle in said computer model until said polarization matrix indicative of polarization properties of said computer model is closely matched to said polarization matrix of said liquid crystal cell under test.

3. A liquid crystal viewing screen tested for defects during manufacture according to the method set forth in claim 2 wherein said calculating a polarization matrix indicative of polarization properties of said computer model further comprises:

representing a cross-section of said computer model of a liquid crystal cell as a plurality of layers of a uniaxial birefringent material, with tilt angle and orientation of each said layer of said plurality of layers varying in a known manner, calculating a polarization matrix for each said layer of said plurality of layers, and from a plurality of polarization matrices developed by said plurality of layers, calculating a composite polarization matrix from said plurality of layers using the formula:

$$M_{cell} = M_Q \cdot M_{Q-1} \cdot \ldots \cdot M_2 \cdot M_1$$

where $M_{cell}$ is the calculated composite Mueller matrix of the liquid crystal cell, and $M_i$ (where i=1 to Q) are the calculated polarization matrices of Q individual layers of said plurality of layers of uniaxial birefringent material representing said cross-section of said computer model of the liquid crystal cell.

4. A liquid crystal viewing screen tested for defects during manufacture according to the method set forth in claim 2 wherein said calculating a polarization matrix indicative of polarization properties of said computer model further comprises:
representing a cross-section of said computer model of a liquid crystal cell as a plurality of layers of a uniaxial birefringent material wherein values for an ordinary and extraordinary refractive index of each layer of said plurality of layers is known,
calculating a polarization matrix for each said layer of said plurality of layers,
from a plurality of polarization matrices developed by said plurality of layers, calculating a composite polarization matrix using the formula:

$$M_{cell} = M_Q \cdot M_{Q-1} \cdot \ldots \cdot M_2 \cdot M_1$$

where $M_{cell}$ is the calculated composite Mueller matrix of the liquid crystal cell, and $M_i$ (where i=1 to Q) are the calculated polarization matrices of Q individual layers of said plurality of layers of uniaxial birefringent material representing said cross-section of said computer model of the liquid crystal cell.

5. A liquid crystal viewing screen tested for defects during manufacture according to the method set forth in claim 2 wherein at least one of said group of estimates of physical parameters of pre-tilt, rubbing direction, cell gap and twist angle for said liquid crystal cell under test are known a priori, and calculating said polarization matrix associated with said liquid crystal cell under test and calculating said polarization matrix associated with said computer model having said known at least one a priori parameter incorporated therein.

6. A liquid crystal viewing screen tested for defects during manufacture according to the method set forth in claim 2 further comprising obtaining a lowest root mean square difference between elements of said polarization matrix indicative of polarization properties of said computer model and said polarization matrix obtained from said polarization properties of said liquid crystal cell under test to determine when said polarization matrix indicative of polarization properties of said liquid crystal cell under test and said polarization matrix indicative of said polarization states from said liquid crystal cell are closely matched.

7. A liquid crystal viewing screen tested for defects during manufacture according to the method set forth in claim 6 further comprising using a Mueller matrix format or a Jones matrix format for each said matrix.

8. A liquid crystal viewing screen tested for defects during manufacture according to the method set forth in claim 6 further comprising calculating said polarization matrix of said liquid crystal cell under test and said polarization matrix of said computer model considering only retardance components for each respective said polarization matrix.

9. A liquid crystal viewing screen tested for defects during manufacture according to the method set forth in claim 8 further comprising:
directing said sequences of polarization states at one or more incident angles and from one or more directions through said liquid crystal cell,
performing a polar decomposition on said polarization matrix of said liquid crystal cell under test,
performing a curve fit on said polarization matrix of said liquid crystal cell under test in order to minimize said root mean square difference between said elements of said polarization matrix indicative of polarization properties of said computer model and corresponding elements of said polarization matrix indicative of said polarization properties of said liquid crystal cell under test.

10. A liquid crystal viewing screen tested for defects during manufacture according to the method set forth in claim 9 further comprising:
displaying an image illustrating trajectory of said polarization properties of said liquid crystal cell under test and said polarization properties of said curve fit on a Poincare sphere, and
providing adjustments for varying a viewing angle of said Poincare sphere.

11. A liquid crystal viewing screen tested for defects during manufacture according to the method set forth in claim 10 further comprising:
allowing a selection of which of said at least one estimated physical parameters of said liquid crystal cell under test are to be measured, and
allowing a priori ones of said at least one estimated physical parameters to be held constant in said computer model.

12. A liquid crystal viewing screen tested for defects during manufacture according to the method set forth in claim 1 further comprising allowing a choice of either a specific location on said liquid crystal cell under test to be measured or automated measurements using a map of predetermined XY coordinates on said liquid crystal cell under test to be measured.

13. A liquid crystal viewing screen tested for defects during manufacture according to the method set forth in claim 1 wherein said D) further comprises:
varying an incident angle, a direction of said incident angle or varying both said incident angle and said direction of said incident angle at which said plurality of polarization states having different orientation, ellipticity and handedness is launched through said liquid crystal cell.

14. A liquid crystal viewing screen tested for defects during manufacture according to the method set forth in claim 1 further comprising:
calculating a plurality of polarization matrices from said sequences of polarization states, and;
developing a composite polarization matrix from said plurality of polarization matrices, said composite polarization matrix indicative of polarization properties of said liquid crystal cell under test.

15. A liquid crystal viewing screen tested for defects during manufacture according to a method using a computer processing device to analyze data representative of measured polarization states of a liquid crystal cell under test to determine at least one physical parameter of said liquid crystal cell under test and comprising:
A) launching a beam of light having a plurality of polarization states through said liquid crystal cell under test, each polarization state of said plurality of polarization states having different orientation, ellipticity and handedness from other said polarization states of said plurality of polarization states,
B) after said plurality of polarization states pass through said liquid crystal cell under test, measuring polarization states as altered by said liquid crystal cell under test at selected points along launched said plurality of polarization states, and converting measured said polarization states into said data representative of said measured polarization states,
C) in a computer processing device, developing a liquid crystal cell model including modeled polarization properties based on at least one estimated physical parameter of said liquid crystal cell under test, D) using said data representative of said measured polarization states, adjusting said computer model until a close match is obtained between said modeled polarization properties and polarization properties of said liquid crystal cell under test, E) whereby when said close match is obtained, said at least one estimated physical parameter of said liquid crystal cell model is indicative of a corresponding said physical parameter of said liquid crystal cell under test.

16. A liquid crystal viewing screen tested for defects during manufacture according to the method set forth in claim 15 wherein said step A) further comprises launching a continuum of time-varying polarization states containing said plurality of polarization states having different orientation, ellipticity and handedness.

17. A liquid crystal viewing screen tested for defects during manufacture according to the method set forth in claim 15 further comprising launching and measuring a sufficient number of said plurality of polarization states having different orientation, ellipticity and handedness to calculate at least a pure retardance matrix.

18. A liquid crystal viewing screen tested for defects during manufacture according to the method set forth in claim 15 further comprising launching and measuring a sufficient number of said plurality of polarization states having different orientation, ellipticity and handedness to allow calculation of a full Mueller or Jones matrix.

19. A liquid crystal viewing screen tested for defects during manufacture according to the method set forth in claim 15 wherein said D) further comprises iteratively adjusting said at least one of said estimated physical parameters of said liquid crystal cell model until a lowest root mean square difference between said polarization properties of said liquid crystal cell model and polarization properties of said liquid crystal cell under test is obtained.

20. A liquid crystal viewing screen tested for defects during manufacture according to the method set forth in claim 19 wherein said D) further comprises varying at least one of said estimated physical parameters comprising cell gap, twist angle, rubbing direction and pre-tilt angle.

21. A liquid crystal viewing screen tested for defects during manufacture according to the method set forth in claim 20 further comprising displaying a varied said at least one estimated physical parameter after said close match is obtained, said at least one closely matched, varied estimated physical parameter representative of a corresponding physical parameter of said liquid crystal cell under test.

22. A liquid crystal viewing screen tested for defects during manufacture according to the method set forth in claim 15 further comprising mounting said liquid crystal cell to an XY translatable stage so that said liquid crystal cell may be moved in X and Y directions to enable measurement at any location on said liquid crystal cell.

23. A liquid crystal viewing screen tested for defects during manufacture according to a method using a computer processor to determine physical parameters of a liquid crystal cell, said method comprising:

A) measuring polarization properties of said liquid crystal cell under test, and converting measured said polarization properties into signals representative of said measured polarization properties of said liquid crystal cell under test, B) In said computer processor, developing a mathematical model of a liquid crystal cell, said mathematical model using estimated physical parameters to model said liquid crystal cell under test, C) using said signals representative of said measured polarization properties of said liquid crystal cell under test, adjusting values in said mathematical model of said liquid crystal cell until a close match is obtained between polarization properties of said mathematical model of a liquid crystal cell and said measured polarization properties of said liquid crystal cell under test, D) providing an indication of quality of said liquid crystal cell under test based on said estimated physical parameters of a closely matched said mathematical model of a liquid crystal cell to said liquid crystal cell under test.

24. A liquid crystal viewing screen tested for defects during manufacture according to the method set forth in claim 23 wherein said A) further comprises:

launching and analyzing a sufficient number of timevarying polarization states each having significantly different orientation, ellipticity and handedness, so as to cover a large portion of a Poincare sphere through said liquid crystal cell under test.

25. A liquid crystal viewing screen tested for defects during manufacture according to the method set forth in claim 24 wherein said B) further comprises:

modeling said liquid crystal cell as a plurality of homogenous layers of a uniaxial birefringent material with known values for ordinary and extraordinary refractive indices of each layer, and wherein orientation and tilt of said layers vary in a known manner, calculating a polarization matrix for each said layer of said homogenous layers, from a plurality of polarization matrices developed from respective said plurality of homogenous layers, calculating a composite polarization matrix for said mathematical model using the formula $$M_{cell} = M_Q \cdot M_{Q-1} \cdot \ldots \cdot M_2 \cdot M_1$$

where $M_{cell}$ is the calculated composite Mueller matrix of the liquid crystal cell, and $M_i$ (where i=1 to Q) are the calculated polarization matrices of Q individual layers of said plurality of layers of uniaxial birefringent material representing said cross-section of said computer model of the liquid crystal cell.

26. A liquid crystal viewing screen tested for defects during manufacture according to the method set forth in claim 25 wherein said C) further comprises iteratively varying one or more mathematical values corresponding to one or more of said estimated physical parameters until said close match is obtained.

27. A liquid crystal viewing screen tested for defects during manufacture according to the method set forth in claim 26 wherein said D) further comprises displaying closely matched said one or more of said estimated physical parameters representative of physical parameters of said liquid crystal cell under test.

28. A liquid crystal viewing screen tested for defects during manufacture according to the method set forth in claim 27 further comprising selecting a repeat ratio between said sequences of polarization states directed at said liquid crystal cell under test and received said sequences of polarization states such that sequential polarization measurements of said liquid crystal cell under test are made with dissimilar said polarization state generator and said polarization state analyzer configurations so that accuracy of said step C) is enhanced.

* * * * *